United States Patent [19]

Goralski et al.

[11] 4,053,633
[45] Oct. 11, 1977

[54] ARYL DIBROMONITROMETHYL SULFONES

[75] Inventors: Christian T. Goralski; Thomas C. Klingler, both of Midland, Mich.

[73] Assignee: The Dow Chemical Company, Midland, Mich.

[21] Appl. No.: 699,546

[22] Filed: June 24, 1976

[51] Int. Cl.$^2$ .................. A01N 9/00; C07C 147/06
[52] U.S. Cl. ........................... 424/337; 71/67; 260/607 AR
[58] Field of Search .............. 260/607 A; 71/67; 162/161; 424/337

[56] References Cited

FOREIGN PATENT DOCUMENTS 1,006,663   4/1957   Germany .................. 260/607 A

OTHER PUBLICATIONS

Chem. Abst. vol. 77, (1972), p. 100997p.
Chem. Abst. (1960), p. 18862i.
Chem. Abst. vol. 49, p. 8176.
J. Org. Chem. vol. 34, (1969), p. 3104–3107.

*Primary Examiner*—Delbert R. Phillips
*Attorney, Agent, or Firm*—Theodore Post; C. Kenneth Bjork

[57] ABSTRACT

Aryl dibromonitromethyl sulfones, new compounds, wherein aryl is phenyl or lower alkyl phenyl, are effective as antimicrobials at a concentration of about 100 parts per million.

6 Claims, No Drawings

ARYL DIBROMONITROMETHYL SULFONES

SUMMARY OF THE INVENTION

This invention concerns aryl dibromonitromethyl sulfones wherein aryl is phenyl or lower alkyl phenyl, and their use as antimicrobials. The compounds are useful at concentrations approximating 100 parts per million (hereinafter ppm), advantageously at a pH of about 5 to about 7. The compounds are used in an aqueous medium which contains a minimum solubilizing amount of an organic solvent such as, for example, acetone, dimethylformamide (hereinafter DMF) or a glycol ether such as, for example, propylene glycol methyl ether, commercially available as Dowanol$^{(R)}$ PM glycol ether. In practice, a stock aqueous solution, for example, containing 0.1 percent total of one or more of the compounds is conveniently prepared containing a minimum solubilizing amount of acetone, DMF or Dowanol$^{(R)}$ PM glycol ether as solvent. The compounds are effective in areas which are subject to antimicrobial attack, particularly slime formation. Among these, an important use is in and about pulp and paper mills. In the specification and claims, lower alkyl designates a 1 to 4 carbon alkyl group.

The compounds are made by mixing and refluxing together a 1:1 mixture of an equimolar proportion of bromonitromethane containing dibromonitromethane as impurity with a sodium arylsulfinate, as defined, in methanol until reaction is complete, about 15 hours. The solvent is removed in vacuo and the residue is taken up in chloroform and water. The organic phase is separated and evaporated to dryness. Recrystallization of the residue from aqueous methanol gives the aryl nitromethyl sulfone. The latter is dissolved in aqueous dilute NaOH, the solution is chilled in ice and bromine is added until the red color persists. After about one hour, the aryl dibromonitromethyl sulfone product is filtered off and recrystallized from aqueous methanol to give purified product. The reaction scheme is represented by the following equation:

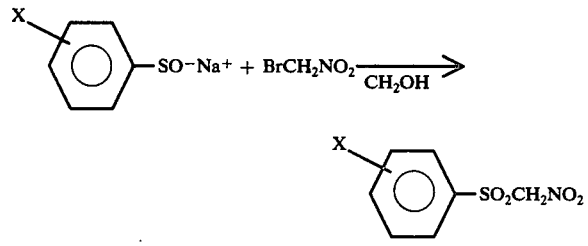

wherein X = H or C$_{1-4}$ alkyl

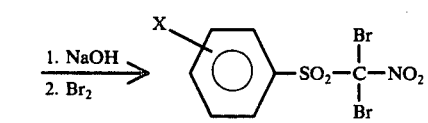

DESCRIPTION OF THE PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1: Dibromonitromethyl p-Tolyl Sulfone

A solution of 22 g of a 1:1 mixture of dibromonitro- and bromonitromethane, and 17.8 g (0.1 mole) of sodium p-toluenesulfinate in 250 ml of methanol was refluxed 15 hours. The solvent was removed in vacuo and the residue taken up in chloroform and water. The organic phase was separated and evaporated to dryness. Recrystallization of the residue from aqueous methanol gave 4 g of nitromethyl p-tolyl sulfone. The latter was dissolved in a solution of 1.6 g of NaOH in 200 ml of water. The solution was chilled in ice and bromine was added thereto until the red color persisted. After one hour, the dibromonitromethyl p-tolyl sulfone product was filtered off and recrystallized from aqueous methanol to give 4.3 g of white crystals: mp 123°–124° C.

Anal. Calcd. for C$_8$H$_7$Br$_2$NO$_4$S: C, 25.76; H, 1.89; Br, 42.85; N, 3.75; S, 8.59. Found: C, 26.74; H, 2.01; Br, 40.00; N, 4.00; S, 9.01.

The procedure of Example 1, when repeated substituting sodium benzenesulfinate in place of sodium p-toluenesulfinate, gives dibromonitromethyl phenyl sulfone.

EXAMPLE 2: Activity of Dibromonitromethyl p-Tolyl Sulfone in Conventional Agar Tests Dibromonitromethyl p-tolyl sulfone in conventional agar tests gave complete kills of the following microorganisms at 100 ppm:
  P. aeruginosa
  E. coli
  C. albicans*
  T. mentagrophytes
  B. subtilis*
  A. aerogenes*
  A. terreus
  C. pelliculosa
  P. pullulans (Aureobasidium pullulans)
  S. typhosa
  Pseudomonas Sp. Strain 10
  M. phlei
  R. nigricans
  Ceratocystis IPS
  C. fragans
  Trichoderm Sp. Madison P-42
  *Slime-forming organisms Dibromonitromethyl phenyl sulfone and the C$_{2-4}$ alkylphenyl homologs of the compound of Example 1 have similar antimicrobial activity. The compounds of this invention may be used separately or in mixtures of two or more to give the advantageous antimicrobial results described above.

What is claimed is:

1. A method for controlling bacteria and fungi by applying to them and to their habitats a cidal amount of a solution containing at least 100 parts per million of an aryl dibromonitromethyl sulfone, wherein aryl represents phenyl or C$_{1-4}$ alkyl-substituted phenyl.

2. Dibromonitromethyl p-tolyl sulfone.

3. Dibromonitromethyl phenyl sulfone.

4. An aqueous mixture useful for preparing a solution for controlling bacteria and fungi consisting essentially of 0.1 percent total of one or more aryl dibromonitromethylsulfones and a solubilizing amount of an organic solvent of the group consisting of acetone, dimethylformamide and propylene glycol methyl ether, the balance being water, wherein aryl represents phenyl or $C_{1-4}$ alkyl-substituted phenyl.

5. An aqueous solution useful for preparing a solution for controlling bacteria and fungi consisting essentially of 0.1 percent of dibromonitromethyl p-tolyl sulfone and a solubilizing amount of an organic solvent of the group consisting of acetone, dimethylformamide and propylene glycol methyl ether, the balance being water.

6. An aqueous solution useful for preparing a solution for controlling bacteria and fungi consisting essentially of 0.1 percent of dibromonitromethyl phenyl sulfone and a solubilizing amount of an organic solvent of the group consisting of acetone, dimethylformamide and propylene glycol methyl ether, the balance being water.

* * * * *